United States Patent [19]

Perraud et al.

[11] Patent Number: 6,022,991

[45] Date of Patent: Feb. 8, 2000

[54] HYDROGEN-FREE REGENERATION OF DITHIOPHOSPHORUS METAL EXTRACTANTS

[75] Inventors: Jean-Jacques Robert Perraud, Mississauga; Dennis Frederick Colton, Carlisle; Jean Paul Duterque, Oakville; Yoshiaki Okita, St. Catherines, all of Canada

[73] Assignees: Cytec Technology Corp., Wilmington, Del.; Compagnie des Mines de Xere (CMX), Paris, France

[21] Appl. No.: 09/207,214

[22] Filed: Dec. 8, 1998

[51] Int. Cl.$^7$ .................................. C07F 9/28; C07F 9/30; C07F 9/38

[52] U.S. Cl. ............................................ 562/9; 423/658.5

[58] Field of Search ....................... 562/8, 9, 23; 423/99, 423/568, 138, 658.5

[56] References Cited

U.S. PATENT DOCUMENTS 5,447,552  9/1995  Mihaylov et al. ........................ 75/722
5,759,512  6/1998  Rickelton et al. ................... 423/658.5

OTHER PUBLICATIONS

Patai, "The Formation and Conversion of Disulphides to Thiols," The chemistry of the thiol group (1974) pp. 220–229.

Advanced Organic Chemistry; Third Edition; J. Wiley & Sons p. 1110. (1985).

Denger et al., Synthesis, Properties and Structure of Bisldialkyldithiophoshinato) manganese (II) Complexes, Inorganica Chimica Acta (1987) pp. 213–215.

Primary Examiner—Gary Geist
Assistant Examiner—Jean F Vollano
Attorney, Agent, or Firm—Blake T. Biederman; Edward A. Steen

[57] ABSTRACT

This is a method of regenerating dithiophosphorus acids from disulfides containing sulfur—sulfur bonds, formed by oxidation of dithiophosphorus acids, such as sulfur—sulfur bonding of dithiophosphoric, dithiophosphonic and dithiophosphinic acids, in a solvent extraction organic phase in which the dithiophosphorus acid is dissolved in a diluent. This process reacts metal directly with the organic solution containing the disulfide to produce a metal loaded complex form of the regenerated dithiophosphorus extractant in the organic solution. This metal complex forms by direct reaction of the metal with the disulfides without requiring the presence or the formation of nascent or gaseous hydrogen. The organic solution containing the regenerated dithiophosphorus extractant can be either directly recycled into a solvent extraction circuit or recycled after the loaded metal is stripped.

18 Claims, 2 Drawing Sheets

HYDROGEN-FREE REGENERATION OF DITHIOPHOSPHORUS METAL EXTRACTANTS

FIELD OF INVENTION

This invention relates to the field of regenerating dithiophosphorus acid solvent extractants from their oxidized forms.

BACKGROUND OF THE INVENTION

Dithiophosphorus acids are useful extractants for the solvent extraction of metal cations. The dithiophosphorus acids of the specification are represented by the following:

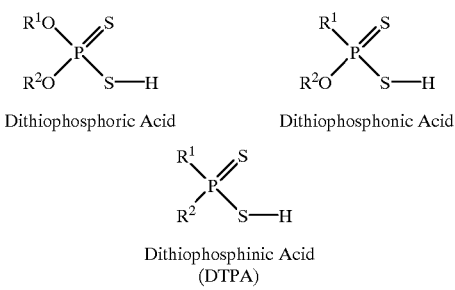

Dithiophosphoric Acid    Dithiophosphonic Acid

Dithiophosphinic Acid
(DTPA)

wherein $R^1$ and $R^2$ are the same or different and are selected from the group consisting of substituted alkyl, cycloalkyl, alkoxyalkyl, alkylcycloalkyl, aryl, alkylaryl, aralkyl and cycloalkylaryl radicals having from about 2 to 24 carbon atoms.

Unfortunately, the dithiophosphorus acid extractants are prone to oxidation during the solvent extraction process. When oxidized, two acid extractant molecules form a sulfur—sulfur bond leading to a disulfide which is incapable of extracting metal cations. These dithiophosphorus acid extractants would not be economic reagents, unless some method of regenerating the active extractant from the disulfide is available.

Rickelton et al., in U.S. Pat. No. 5,759,512 ('512), disclose a process that relies upon active nascent hydrogen to break the sulfur—sulfur bond of the disulfide and regenerate the acid extractant. For example, this process adds zinc powder to an agitated mixture of sulfuric acid solution and the solvent extractant organic solution, generating nascent hydrogen for the extractant regeneration such that all the metal is finally dissolved. Although relatively costly, this regeneration improves the economics of recovering metals with dithiophosphorus extractants, since the partially oxidized extractant solution can be regenerated and, therefore, the original metal loading capacity can be restored.

Specifically, the process of the '512 patent relies upon either nascent hydrogen formed from reacting a metal with a strong acid in aqueous phase or from bubbled hydrogen in the presence of a catalyst. Unfortunately, these processes generate large quantities of unreacted hydrogen gas that require special equipment and precautions to prevent explosions. Furthermore, the nascent hydrogen processes, such as the zinc-sulfuric acid process, require neutralization and disposal of an acidic waste product. Moreover, the metal consumption described in the '512 patent is much larger than what appears to be required by the extractant regeneration stoichiometry, suggesting a poor efficiency of the nascent hydrogen towards regeneration versus hydrogen gas formation.

Denger et al., in "Synthesis, Properties and Structure of Bis (dialkyldithiophosphinato) manganese (II) Complexes," *Inorganica Chemica Acta*, 132 (1987), disclose reacting powdered manganese with bis(diorganothiophosphoryl) disulf[ide] to form laboratory scale quantities of a manganese (II) dithiophosphinate for x-ray crystallographic studies.

It is an object of the invention to provide a process that regenerates disulfides formed by oxidation of dithiophosphorus acids without reliance upon nascent hydrogen or a catalyst.

It is a further object of the invention to provide a method of regenerating the disulfides formed by oxidation of dithiophosphorus acids without the necessity of having to dispose of an acidic waste stream.

It is a further object of the invention to reduce the amount of metal consumed during regeneration, thereby resulting in a lower cost process.

SUMMARY OF THE INVENTION

A process for the regeneration of organic dithiophosphorus extractant degraded in a solvent extraction process that allows a much longer life expectancy of the extractant mixture. The degraded organic phase consists of an organic solution containing undegraded dithiophosphorus acid, and sulfur—sulfur bonded structures formed from two dithiophosphorus acid molecules, all present in a diluent used in a solvent extraction circuit. This process regenerates dithiophosphorus acids (i.e. dithiophosphinic acids, dithiophosphonic acids and dithiophosphoric acids) by contacting the organic phase with metal. The disulfide reacts directly with the metal and produces a metal complex of the regenerated dithiophosphorus extractant in the organic solution. This metal complex forms without the presence of or the formation of hydrogen. The organic solution containing the regenerated dithiophosphorus extractant can be either directly recycled into a solvent extraction circuit or recycled after the loaded metal is stripped.

DESCRIPTION OF PREFERRED EMBODIMENT

Figure 1:
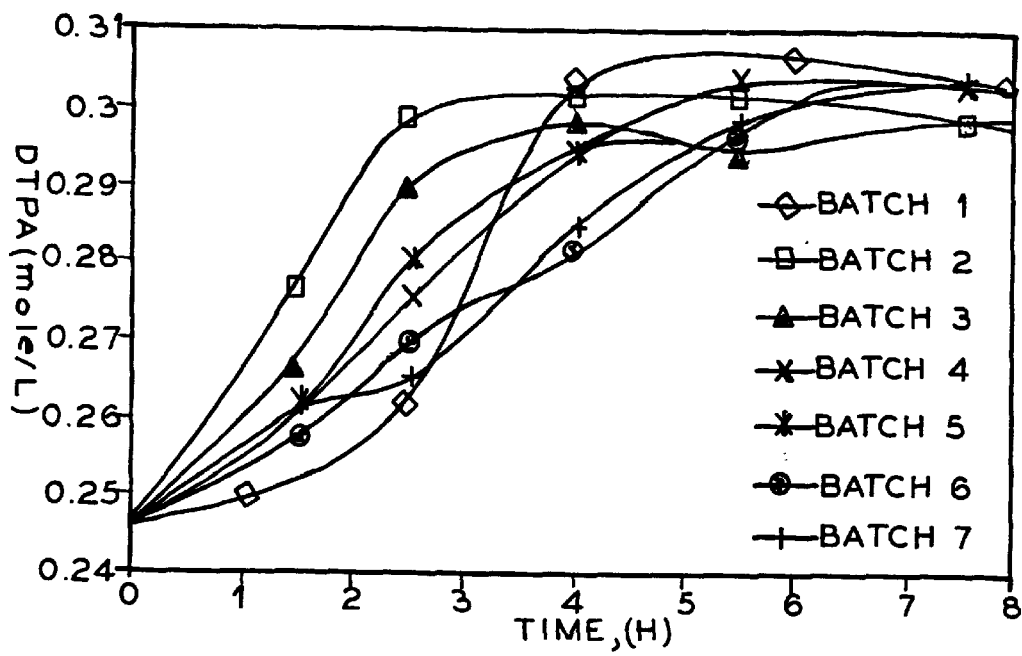
FIG. 1 plots DTPA concentrations as a function of time for seven batches regenerated with the same initial batch of nickel powder.

This process transforms disulfides, which are formed in the organic solution by oxidation of the dithiophosphorus acid, back into the metal loaded form of the dithiophosphorus acid by contacting the organic solution with a metal. Any sacrificial metal which can form a complex with dithiophosphorus acids reacts directly to reduce the sulfur—sulfur bond of the disulfide in the absence of nascent or gaseous hydrogen. The metal itself is therefore oxidised to metal ions and the disulfide is transformed back into the metal loaded form of the dithiophosphorus acid, which is the end product of the reaction.

The presence of aqueous solution or water advantageously acts as an accelerating agent for the reaction. The amount of water required to accelerate the reaction is very small. Even the water entrained in the organic phase after a normal aqueous/organic phase separation in a solvent extraction circuit is sufficient. Alternatively, a separating agent such as water or aqueous solution can be added to the regeneration system to facilitate separation between the organic phase and unreacted metal. After agitation of the system ceases, unreacted metal settles in the water or aqueous phase to allow easy separation from the organic phase.

In regenerating dithiophosphinic acids, a metal powder reacts to form an intermediate of Bis(dithiophosphinato)-metal complex. Advantageously, the metal consists of a cobalt, iron, manganese, nickel or zinc powder or any metal which forms a complex with dithiophosphorus acids. The regeneration reaction proceeds under an air atmosphere, but since air is an oxidizing agent, an inert atmosphere advantageously improves the regeneration. Acceptable atmospheres include the Group VIII gases, $CO_2$, $N_2$ and any other gases non-reactive with the process. The following illustrates the regeneration process for a dithiophosphinic extractant using nickel metal:

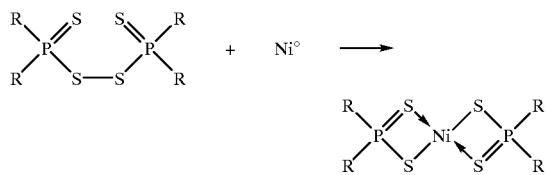

The Bis(dithiophosphinato)-nickel(II) complex product formed is similar to the product formed during the metal ion solvent extraction step—strong acids strip the metal to convert the complex back into its free extractant acid form. Thus, re-injecting this complex directly back into a nickel solvent extraction circuit allows regeneration without the requirement for additional vessels or reagents for stripping the metal and neutralizing effluent streams. In a nickel solvent extraction circuit for example, this Bis (dithiophosphinato)-nickel(II) complex releases its loaded nickel cation with a strong acid, providing free DTPA extractant for further loading, as follows:

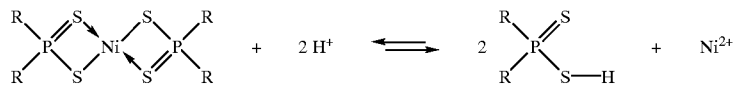

The regeneration reaction occurs at about room temperature (20° C.) to 95° C. Increasing temperature to at least about 40° C. accelerates the reaction. To avoid volatilization of any diluent present with the organic phase, the reaction advantageously occurs at a temperature of less than about 80° C. Although it is most advantageous to have the reaction occur in the presence of a diluent, it is not considered essential that a diluent be present.

Since this process is a surface area dependent process, it is advantageous but not necessary to use metal in its powder form for increasing reaction efficiency. Advantageously, the powder has a specific surface area of at least about 0.001 $m^2/g$. Most advantageously, the powder has at least about a 0.005 $m^2/g$ specific surface area. Furthermore, the use of excess metal advantageously promotes the reaction to proceed at an acceptable rate. However, the excess metal can be reused to treat additional batches of degraded organic solution, decreasing dramatically the overall metal consumption.

EXAMPLES

Example 1

A 15% (vol.) Cyanex 301, (bis(2,4,4trimethylpentyl) dithiophosphinic acid, a registered product of Cytec Industries Inc.), solution in Isopar M diluent (an aliphatic solvent from Imperial Oil), degraded to 58% of its original metal loading capacity, provided the test sample. A 1,000 mL heated vessel containing baffles and a 550 rpm down-draft agitating impeller provided the reactor. Introducing 250 mL of the test sample in the reactor established the regeneration mixture. The reaction proceeded with agitation under a $CO_2$ atmosphere and a temperature set point of 65° C. After reaching the temperature set point, adding 25 g of nickel-123 powder, a registered product of INCO Ltd (specific surface area of 0.34 to 0.44 $m^2/g$) initiated the reaction. Organic samples were taken from the reactor at regular intervals. Stripping the regenerated nickel loaded organic samples with HCl 6N provided nickel(II) free organic samples. Analysing the organic samples for free DTPA by acid titration showed that the extractant capacity increased as a function of time from less than 60% to more

TABLE 1

| Time (h) | [DTPA] (mole/L) | Capacity (%) |
|---|---|---|
| 0 | 0.190 | 58 |
| 3 | 0.262 | 79 |
| 6 | 0.289 | 86 |

Note: Fresh 15% solution of Cyanex 301 has a free DTPA concentration of 0.33 mole/L.

Example 2

Effect of Addition of Water

This test operated with the conditions and equipment of Example 1, except that the organic solution had 55% loading capacity and the reactor contained an additional 25 mL of water. The assays of Table 2 show that the extractant capacity increased as a function of time from less than 60% to more than 95% after 4 hours.

TABLE 2

| Time (h) | [DTPA] (mole/L) | Capacity (%) |
|---|---|---|
| 0 | 0.194 | 59 |
| 2 | 0.242 | 73 |
| 4 | 0.315 | 95 |
| 6 | 0.323 | 98 |

EXAMPLE 3

Recycle of Nickel Powder

A solution of 15% (vol.) Cyanex 301 solution in Isopar M, degraded to 74% loading capacity provided the test sample. The organic contained 1.5 g/L of nickel(II). A 50 L fiberclass resin (FRP) reactor vessel with baffles, agitated with a down-draft impeller at 300 rpm, was used. A water jacket heated the test sample. Introducing 40 L of the degraded organic test sample and 5 L of water into the agitated reactor under a $CO_2$ atmosphere established the regeneration mixture. After reaching the temperature set point of 65° C., adding 4 kg of nickel-123 powder initiated the reaction. Organic samples were taken from the reactor at regular intervals. Stripping the regenerated nickel loaded organic samples with HCl 6N provided nickel(II) free organic samples. Stopping the agitation after 10 h allowed the aqueous solution and solids to settle to the bottom of the reactor. After one hour of settling, the organic solution was removed from the reactor without disturbing the solids settled in an aqueous layer.

Pouring a second batch of 40 L degraded organic (at 65° C.) into the reactor re-established the regeneration reaction without adding additional nickel powder. Repeating this procedure for seven successive batches (with the same nickel powder) regenerated each batch of degraded extractant. Stripping the regenerated Ni loaded organic samples with HCl 6N provided nickel(II) free organic samples and the data of FIG. 1.

The assays of FIG. 1 demonstrate that the extractant capacity increased as a function of time from less than 75% to more than 88% after 5 hours in all successive batches that used recycled nickel powder.

EXAMPLE 4

Effect of Temperature

Figure 2:
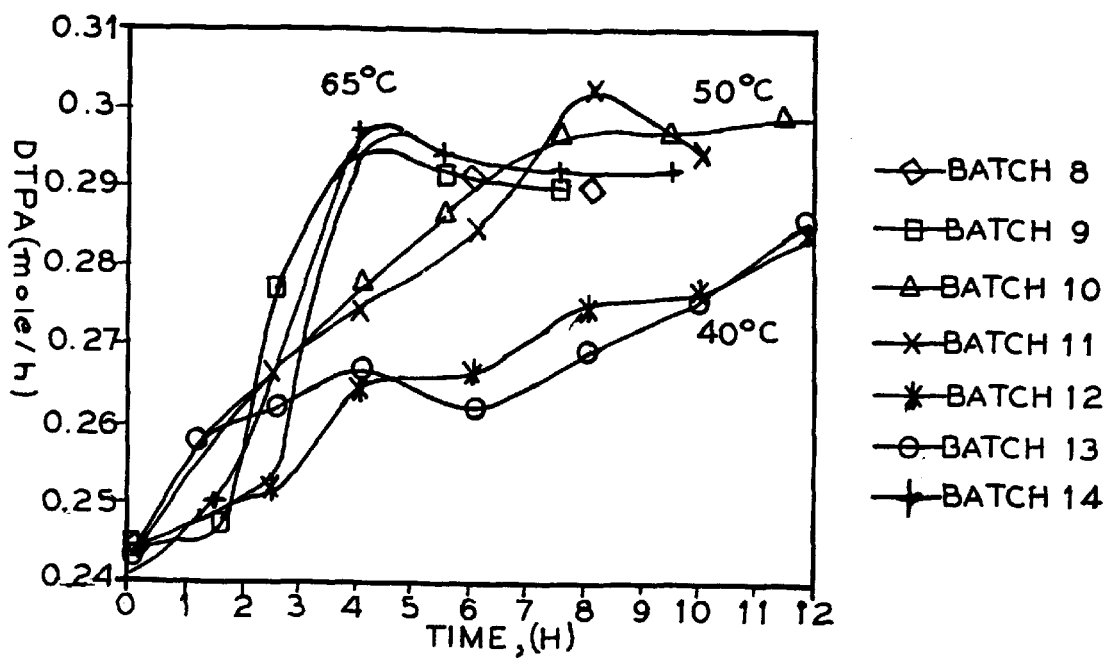
FIG. 2 shows the effect of temperature (40° C., 50° C. and 65° C.) on DTPA regeneration rate.
Figure 3:
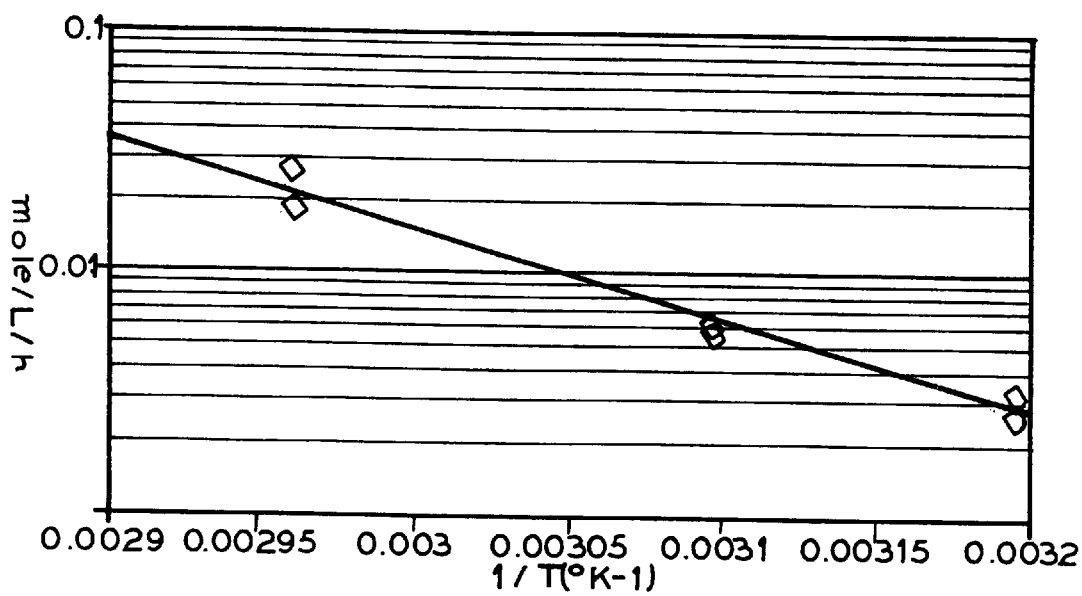
FIG. 3 plots regeneration rate as a logarithmic function of temperature.

A second series of seven batches followed the procedure described in Example 3 at various temperature set points: Batch Nos. 8, 9 and 14 at 65° C.; Batch Nos. 10 and 11 at 50° C. and Batch Nos. 12 and 13 at 40° C. The assays of FIGS. 2 and 3 show that the extractant metal loading capacity increased at different rates as a function of the temperature. The activation energy $[-R\Delta(\ln k)/\Delta(1/T)]$ equaled 69 KJ/mol.

EXAMPLE 5

Continuous Regeneration

Figure 4:
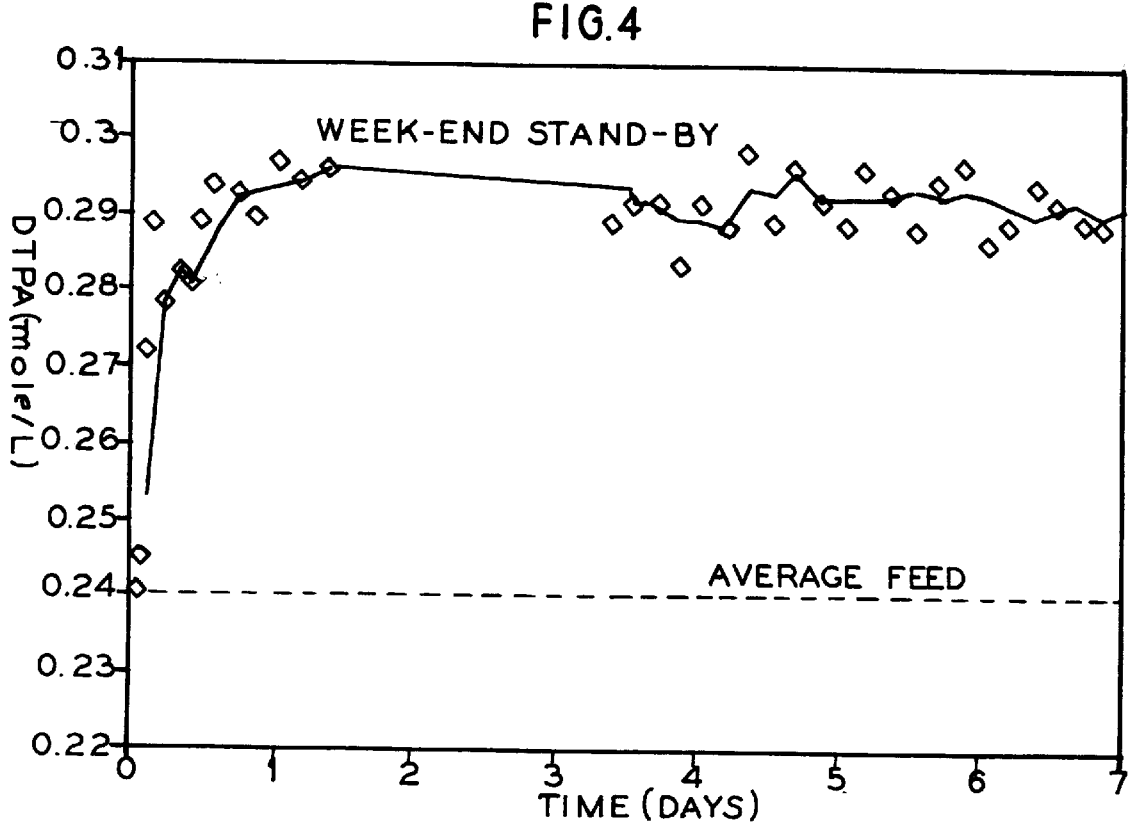
FIG. 4 shows continuous regeneration of DTPA over a seven day period.

In this test, the test sample of Examples 3 and 4 was regenerated in a continuous process. The equipment consisted of a 22 L, stirred, water-jacketed, reaction chamber and a 12 L settling tank; both of them held under a $CO_2$ atmosphere. A down-draft impeller, at 250 rpm, provided agitation in the reaction chamber. The reactor was initially filled with the degraded organic. After reaching the 65° C. temperature set point, introducing 2.5 kg of nickel-123 powder initiated the regeneration reaction. After 6 h of batch-type reaction, a continuous supply of degraded organic was started. The 65° C. water-jacketed reaction vessel was fed with degraded organic at a rate of 4.2 L/h. Adding 250 g of nickel 123 powder on a daily basis supplied the reactor vessel with a fresh supply of nickel. Stripping and analysing samples every four hours for free DTPA as before proved the continuous regeneration. The assays plotted in FIG. 4 show that the extractant metal loading capacity of the product increased to an average of 88% from an initial 73% metal loading capacity. The average product contained 0.29 mol/L DTPA with a total of 4.75 mole DTPA produced each day. The reaction consumed 3.75 kg of nickel during the entire several day test to regenerate 625 liters of feed solution.

EXAMPLE 6

Zinc Powder

A 15% (vol.) Cyanex 301 solution in Isopar M, degraded to 49% of its original metal loading capacity, provided the test sample. The equipment and procedure was similar to that of Example 1 except that it relied upon 25 g of fine zinc powder (4 $\mu$m) to regenerate the DTPA. Removing organic samples every 1.5 h provided assays for testing in accordance with the procedure of example 1. The assays in Table 3 showed that the extractant capacity increased as a function of time from less than 50% to 75% after 6 hours.

TABLE 3

| | [DTPA] | |
|---|---|---|
| Time (h) | (mole/L) | Capacity (%) |
| 0 | 0.163 | 49 |
| 1.5 | 0.207 | 63 |
| 3 | 0.215 | 65 |
| 4.56 | 0.230 | 70 |
| 6 | 0.249 | 75 |

EXAMPLE 7

Iron Powder

A 15% (vol.) Cyanex 301 solution in Isopar M, degraded to 57% of its original metal loading capacity, provided the test sample. The equipment and procedure was similar to that of Example 1, excepted that it relied upon 50 g of iron powder (–250 $\mu$m, Domfer MP-61) to regenerate the DTPA. Removing organic samples every one hour provided assays for testing in accordance with the procedure of Example 1. The assays in Table 4 showed that the extractant capacity increased as a function of time from less than 60% to almost 90% after 2 hours.

TABLE 4

| | [DTPA] | |
|---|---|---|
| Time (h) | (mole/L) | Capacity (%) |
| 0 | 0.187 | 57 |
| 1 | 0.253 | 77 |
| 2 | 0.290 | 88 |
| 4.5 | 0.288 | 87 |
| 6 | 0.249 | 75 |

For a nickel solvent extraction circuit, the degraded organic solution of 15% vol. DTPA in an aliphatic diluent most advantageously reacts in the presence of water with 100 g of nickel-123 powder per litre of organic solution—it is most advantageous to match the metal powder with an end-product of a solvent extraction circuit. This reaction most advantageously occurs at a temperature of 65° C., with an organic to aqueous ratio of 10 to 20 and under a protective $CO_2$ atmosphere. This reaction forms a nickel complex in 4 to 6 hours depending on the level of degradation of the organic reagent. Recycling any remaining nickel powder in the reactor limits adding of fresh nickel to the previous regeneration's consumption.

This process operates effectively in a batch or a continuous mode. In the batch process, after the reaction, the bulk of remaining nickel powder settles quickly in an aqueous solution to allow the filtration of entrained micron-size metallic particles before the re-introduction of the regenerated organic extractant solution into the solvent extraction circuit. In the continuous process, adjusting flow rates and reaction time of the organic with a metal powder can achieve steady-state extractant concentrations in solvent extraction circuits.

This process has several advantages over the earlier method for regenerating dithiophosphorus acids. First, this process avoids the generation of large quantities of hydrogen. Second, this process does not require the addition or disposal of acidic reagents. Third, this process allows matching of a solvent extraction circuit's product with the sacrificial metal used. Fourth, this process more efficiently regenerates the dithiophosphorus acids, than the nascent hydrogen processes. Finally, the process can use a solvent extraction circuit's stripping stage to form the dithiophosphorus acid from the cation-loaded organic.

In accordance with the provisions of the statute, this specification illustrates and describes specific embodiments of the invention. Those skilled in the art will understand that the claims cover changes in the form of the invention and that certain features of the invention may operate advantageously without a corresponding use of the other features.

We claim:

1. A process of regenerating oxidized dithiophosphorus acids comprising the steps of:
   a) providing an organic solution, said organic solution containing a disulfide formed by oxidation and sulfur—sulfur bonding of an extractant selected from the group consisting of dithiophosphoric acid, dithiophosphonic acid and dithiophosphinic acid,
   b) contacting said organic solution with a metal selected from the group consisting of cobalt, iron, manganese, nickel and zinc, and
   c) reacting said metal with said disulfide in said organic solution to break the sulfur—sulfur bond in the disulfide and form a metal complex with the dithiophosphorus acid, said metal complex forming with said organic solution free of nascent hydrogen and gaseous hydrogen.

2. The process of claim 1 including the additional step of returning said metal complex to a solvent extraction circuit.

3. The process of claim 1 including the additional steps of stripping said metal complex with an acid to produce a free dithiophiosphorus acid extractant and returning said free dithiophosphorus acid extractant to a solvent extraction circuit.

4. The process of claim 1 including the additional step of agitating said organic solution during said reacting of said extractant.

5. The process of claim 1 including the additional step of using a separating agent selected from the group consisting of an aqueous solution and water to separate regenerated extractant in said organic solution from metal not reacted in step c.

6. The process of claim 1 wherein said metal reacted with said organic solution is recovered with said extractant in a solvent extraction circuit.

7. The process of claim 1 wherein said reacting form said metal complex with a sacrificial metal to regenerate dithiophosphinic acid extractant, said sacrificial metal being selected from the group consisting of cobalt and nickel; and including the additional step of introducing said metal complex into a solvent extraction circuit to recover said sacrificial metal.

8. The process of claim 1 wherein said metal has a specific surface area of at least about 0.001 $m^2/g$.

9. The process of claim 1 wherein said metal complex forms at a temperature between about 20° C. and 95° C.

10. A process of regenerating oxidized dithiophosphorus acids comprising the steps of:
    a) providing a mixture of an accelerating agent and an organic solution, said accelerating agent being selected from the group consisting of aqueous solution and water, said organic solution containing a disulfide formed by oxidation and sulfur—sulfur bonding of an extractant selected from the group consisting of dithiophosphoric acid, dithiophosphonic acid and dithiophosphinic acid,
    b) contacting said mixture of accelerating agent and organic solution with a metal selected from the group consisting of cobalt, iron, manganese nickel and zinc, and
    c) reacting said metal with said disulfide in said mixture of accelerating agent and organic solution to break the sulfur—sulfur bond in the disulfide and form a metal complex with the dithiophosphorus acid, said metal complex forming with said mixture of accelerating agent and organic solution free of nascent hydrogen.

11. The process of claim 10 including the additional step of returning said metal complex to a solvent extraction circuit.

12. The process of claim 10 including the additional steps of stripping said metal complex with an acid to produce the free dithiophosphorus acid extractant and returning said free dithiopliosphorus acid extractant to a solvent extraction circuit.

13. The process of claim 10 including the additional step of agitating said organic solution during said reacting of said extractant.

14. The process of claim 10 including the additional step of using a separating agent selected from the group consisting of an aqueous solution and water to separate regenerated extractant in said organic solution from metal not reacted in step c.

15. The process of claim 10 wherein said metal reacted with said organic solution is recovered with said extractant in a solvent extraction circuit.

16. The process of claim 10 wherein said reacting forms a metal complex with a sacrificial metal to regenerate dithiophosphinic acid extractant, said sacrificial metal being selected from the group consisting of cobalt and nickel; and including the additional step of introducing said metal complex into a solvent extraction circuit to recover said sacrificial metal.

17. The process of claim 10 wherein said metal has a specific surface area of at least about 0.001 $m^2/g$.

18. The process of claim 10 wherein said metal complex forms at a temperature between about 20° C. and 95° C.

* * * * *